United States Patent
Rabel et al.

(10) Patent No.: US 6,225,317 B1
(45) Date of Patent: May 1, 2001

(54) CRYSTALLINE (−)-6-CHLORO-4-CYCLOPROPYLETHYNYL-4-TRIFLUOROMETHYL-3,4-DIHYDRO-2(1H)-QUINAZOLINONE

(75) Inventors: Shelley R. Rabel, Landenberg, PA (US); Mona Patel; Rodney Lawrence Parsons, Jr., both of Wilmington, DE (US)

(73) Assignee: DuPont Pharmaceuticals Company, Wilmington, DE (US)

( * ) Notice: Subject to any disclaimer, the term of this patent is extended or adjusted under 35 U.S.C. 154(b) by 0 days.

(21) Appl. No.: 09/442,605

(22) Filed: Nov. 18, 1999

Related U.S. Application Data (60) Provisional application No. 60/109,244, filed on Nov. 19, 1998.

(51) Int. Cl.[7] .................. C07D 234/72; A61K 31/517
(52) U.S. Cl. ...................... 514/259; 544/286; 544/283
(58) Field of Search .................. 514/259; 544/286, 544/283

(56) References Cited

U.S. PATENT DOCUMENTS 6,124,302 * 9/2000 Corbett et al. ................ 514/259

FOREIGN PATENT DOCUMENTS

9845276 * 10/1998 (WO) .
9950253 * 10/1998 (WO) .
9950253   10/1999 (WO) .

* cited by examiner

Primary Examiner—Mukund J. Shah
Assistant Examiner—Sudhaker B. Patel (57) ABSTRACT

The potent reverse transcriptase inhibitor (−)-6-Chloro-4-cyclopropylethynyl-4-trifluoromethyl-3,4-dihydro-2(1H)-quinazolinone is produced in solvate and crystalline form. These forms are designated Forms 1 and 2, and are characterized by x-ray powder diffraction and differential scanning calorimetry. Pharmaceutical compositions and methods are useful for the treatment of the human immunodeficiency virus (HIV).

24 Claims, 4 Drawing Sheets

CRYSTALLINE (-)-6-CHLORO-4-CYCLOPROPYLETHYNYL-4-TRIFLUOROMETHYL-3,4-DIHYDRO-2(1H)-QUINAZOLINONE

This application claims the benefit of U.S. Provisional Application No. 60/109,244, filed Nov. 19, 1998.

FIELD OF THE INVENTION

The potent reverse transcriptase inhibitor (-)-6-Chloro-4-cyclopropylethynyl-4-trifluoromethyl-3,4-dihydro-2(1H)-quinazolinone is produced in solvate and preferred crystalline form. These forms are designated Forms 1 and 2, respectively, and characterized by x-ray powder diffraction and differential scanning calorimetry. Pharmaceutical compositions and methods are useful for the treatment of the human immunodeficiency virus (HIV).

BACKGROUND OF THE INVENTION

Reverse transcription is a common feature of retrovirus replication. Viral replication requires a virally encoded reverse transcriptase to generate DNA copies of viral sequences by reverse transcription of the viral RNA genome. Reverse transcriptase, therefore, is a clinically relevant target for the chemotherapy of retroviral infections because the inhibition of virally encoded reverse transcriptase would interrupt viral replication.

An extremely promising and active area of research is in the discovery of non-nucleoside HIV reverse transcriptase inhibitors. Quinazolinones represent a class of compounds which have been found to be useful non-nucleoside based inhibitors of HIV reverse transcriptase. Commonly assigned U.S. patent application Ser. No. 09/056,820 discloses the novel quinazolinone (-)-6-Chloro-4-cyclopropylethynyl-4-trifluoromethyl-3,4-dihydro-2(1H)-quinazolinone as a particularly active non-nucleoside inhibitor of HIV reverse transcriptase with efficacy against HIV reverse transcriptase resistance.

(-)-6-Chloro-4-cyclopropylethynyl-4-trifluoromethyl-3,4-dihydro-2(1H)-quinazolinone is represented structurally as formula (I):

(I)

Solvate and crystalline forms of (I) have not been known to exist previously. The discovery of such forms which exhibit chemical and physical advantages for manufacture, purification, and formulation are necessary for feasible commercialization of (I).

Treatment or prevention of the foregoing disorders is accomplished by administering a therapeutically effective amount of the solvate or crystalline form of compound (I) to a human or animal subject in need of such treatment or prevention. Treatment with such forms of compound (I) may be accomplished by its use as a single compound, as a pharmaceutical composition ingredient, or in combination with other antivirals, immunomodulators, antibiotics and vaccines. The compound may be administered enterally or parenterally in solid or liquid dosage forms.

SUMMARY OF THE INVENTION

In one aspect, the present invention is directed to solvate and crystalline forms of (-)-6-Chloro-4-cyclopropylethynyl-4-trifluoromethyl-3,4-dihydro-2(1H)-quinazolinone (I). A related aspect resides in novel solvate forms and crystalline forms of (I), designated Form 1 and Form 2, respectively. Form 1 has been characterized by differential scanning calorimetry (DSC), powder x-ray diffraction analysis (XRD), and nuclear magnetic resonance spectroscopy (NMR). Form 2 has been characterized by differential scanning calorimetry (DSC), and powder x-ray diffraction analysis (XRD).

Further aspects of the invention involve pharmaceutical compositions of (-)-6-Chloro-4-cyclopropylethynyl-4-trifluoromethyl-3,4-dihydro-2(1H)-quinazolinone in its forms. The Forms of this invention may be formulated into conventional solid pharmaceutical dosage forms or used for the preparation of liquid dosage forms by combining a therapeutically effective amount of the forms of the drug with a pharmaceutically acceptable carrier. The Forms may be administered in pharmaceutical compositions which may combine other antivirals, immunomodulators, antibiotics or vaccines.

In another aspect, the present invention involves a method for inhibiting reverse transcriptase which comprises administering an amount of Form 1 or Form 2 of (-)-6-Chloro-4-cyclopropylethynyl-4-trifluoromethyl-3,4-dihydro-2(1H)-quinazolinone, sufficient to result in reverse transcriptase being contacted with an effective inhibitory amount of the active drug substance. In particular aspects, the invention involves methods for treating retroviral infections such as human immunodeficiency virus and disorders involving viral replication, which comprise administering a therapeutically effective amount of a pharmaceutical composition comprising the novel forms of this invention.

It is another object of the present invention to provide a novel method for treating HIV infection which comprises administering to a host in need thereof a therapeutically effective combination of (-)-6-Chloro-4-cyclopropylethynyl-4-trifluoromethyl-3,4-dihydro-2(1H)-quinazolinone existing as Forms 1 or 2, with one or more compounds selected form the group consisting of HIV reverse transcriptase inhibitors and HIV protease inhibitors.

BRIEF DESCRIPTION OF THE DRAWINGS

The invention is illustrated by reference to the accompanying drawings described below.

DETAILED DESCRIPTION OF THE INVENTION

In a first embodiment, the present invention provides solvates of (−)-6-Chloro-4-cyclopropylethynyl-4-trifluoromethyl-3,4-dihydro-2(1H)-quinazolinone.

In a preferred embodiment, the solvate is the methanol solvate of (−)-6-Chloro-4-cyclopropylethynyl-4-trifluoromethyl-3,4-dihydro-2(1H)-quinazolinone, and is in substantially pure form.

In a more preferred embodiment, the methanol solvate of (−)-6-Chloro-4-cyclopropylethynyl-4-trifluoromethyl-3,4-dihydro-2(1H)-quinazolinone is characterized by an x-ray powder diffraction pattern comprising two or more 2θ values selected from the group consisting of: 9.26±0.2, 12.00±0.2, 15.02±0.2, 23.52±0.2, and 24.08±0.2.

Figure 1:
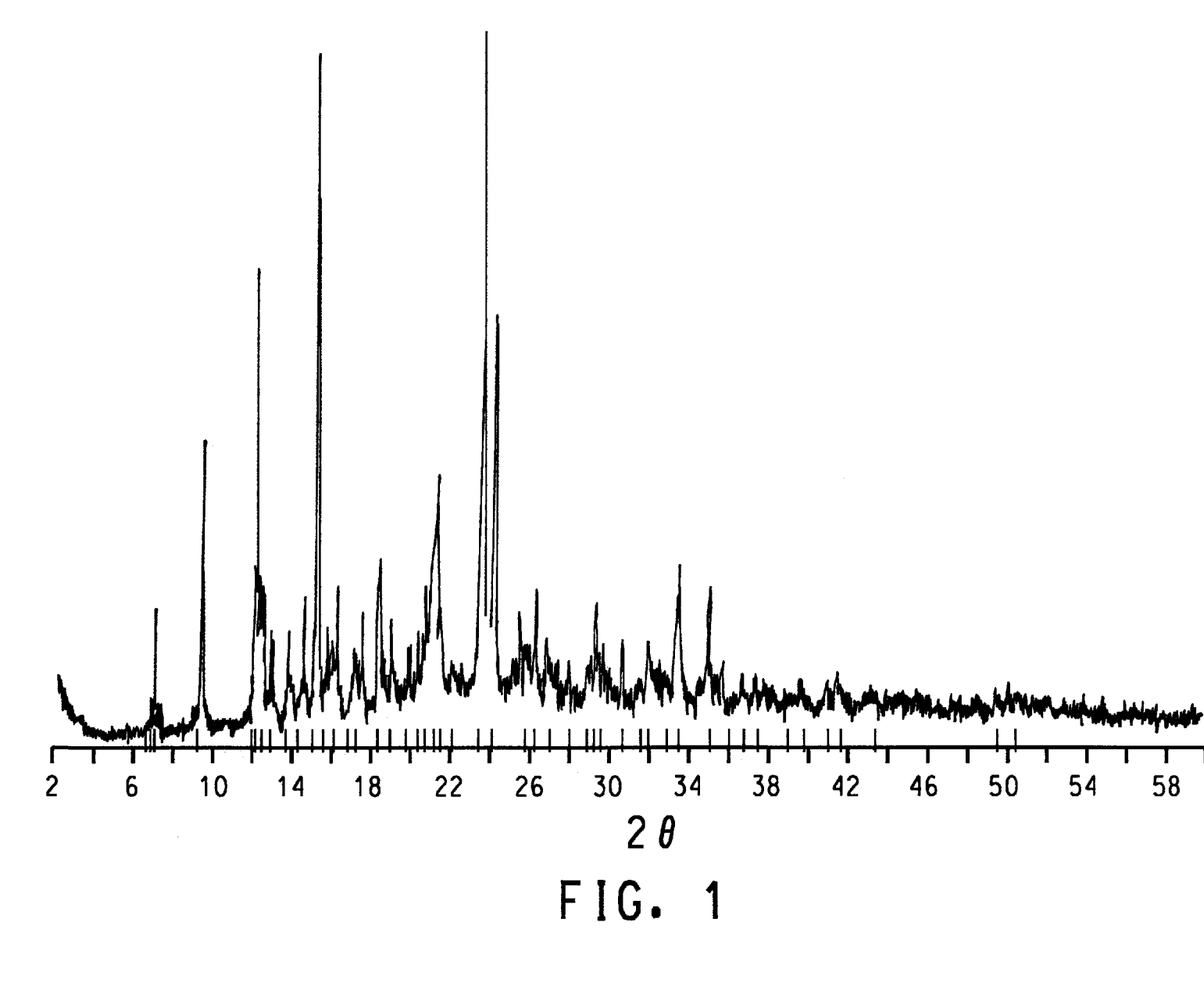
FIG. 1 shows a powder x-ray diffractogram of Form 1, the methanol solvate of (-)-6-Chloro-4-cyclopropyl-ethynyl-4-trifluoromethyl-3,4-dihydro-2(1H)-quinazolinone.

In another more preferred embodiment, the methanol solvate of (−)-6-Chloro-4-cyclopropylethynyl-4-trifluoromethyl-3,4-dihydro-2(1H)-quinazolinone is characterized by an x-ray powder diffraction pattern substantially in accordance with that shown in FIG. 1.

In another more preferred embodiment, the methanol solvate of (−)-6-Chloro-4-cyclopropylethynyl-4-trifluoromethyl-3,4-dihydro-2(1H)-quinazolinone is characterized by a differential scanning calorimetry thermogram exhibiting an endothermic transition at about 90° C. to about 110° C.

In an even more preferred embodiment, the methanol solvate of (−)-6-Chloro-4-cyclopropylethynyl-4-trifluoromethyl-3,4-dihydro-2(1H)-quinazolinone is characterized by an x-ray powder diffraction pattern comprising two or more 2θ values selected from the group consisting of: 9.26±0.2, 12.00±0.2, 15.02±0.2, 23.52±0.2, and 24.08±0.2, and further characterized by a differential scanning calorimetry thermogram exhibiting an exothermic transition at 90° C. to about 110° C.

In another even more preferred embodiment, the nuclear magnetic resonance spectrum of the methanol solvate has a singlet peak at about 3.49 ppm.

In a second embodiment, the present invention describes a pharmaceutical composition comprising a therapeutically effective amount of the methanol solvate of (−)-6-Chloro-4-cyclopropylethynyl-4-trifluoromethyl-3,4-dihydro-2(1H)-quinazolinone and a pharmaceutically acceptable carrier.

In a preferred embodiment, the pharmaceutical composition is contained in a capsule or compressed tablet dosage form, wherein the therapeutically effective amount is about 1 mg to about 1000 mg of the methanol solvate of (−)-6-Chloro-4-cyclopropylethynyl-4-trifluoromethyl-3,4-dihydro-2(1H)-quinazolinone.

In a more preferred embodiment, the pharmaceutical composition is contained in a capsule or compressed tablet dosage form, wherein the therapeutically effective amount is about 50 mg to about 200 mg of the methanol solvate of (−)-6-Chloro-4-cyclopropylethynyl-4-trifluoromethyl-3,4-dihydro-2(1H)-quinazolinone.

In another more preferred embodiment, the pharmaceutical composition contained in a capsule or compressed tablet contains greater than about 10% by weight of a disintegrant relative to the total dry weight of the dosage form.

In another preferred embodiment, the pharmaceutical composition is in liquid form.

In a more preferred embodiment, the liquid form comprises about 0.1 percent to about 15 percent by weight of the methanol solvate of (−)-6-Chloro-4-cyclopropyl-ethynyl-4-trifluoromethyl-3,4-dihydro-2(1H)-quinazolinone and a liquid vehicle comprising about 50 percent to about 99 percent by weight of polyolesters of medium chain fatty acids.

In an even more preferred embodiment, the composition is contained in a soft gelatin capsule, wherein the polyolesters of medium chain fatty acids consist essentially of $C_8$ to $C_{10}$ fatty acid triglycerides.

In another more preferred embodiment, the liquid form comprising about 0.1 percent to about 15 percent by weight of the methanol solvate of (−)-6-Chloro-4-cyclopropylethynyl-4-trifluoromethyl-3,4-dihydro-2(1H)-quinazolinone and a liquid vehicle comprising about 50 percent to about 99 percent by weight of polyolesters of medium chain fatty acids contains a sweetening agent in a range of about 0.1 percent to about 50 percent by weight.

In another more preferred embodiment, the pharmaceutical composition which is in liquid form comprises about 0.1 percent to about 10 percent by weight of the methanol solvate of (−)-6-Chloro-4-cyclopropylethynyl-4-trifluoromethyl-3,4-dihydro-2(1H)-quinazolinone and a liquid vehicle about 50 percent to about 99 percent by weight of vegetable oil.

In an even more preferred emobodiment, the pharmaceutical composition is contained in a soft gelatin capsule, wherein the vegatable oil is soybean oil or peanut oil.

In another more preferred embodiment, the pharmaceutical composition which is in liquid form comprising about 0.1 percent to about 10 percent by weight of the methanol solvate of (−)-6-Chloro-4-cyclopropylethynyl-4-trifluoromethyl-3,4-dihydro-2(1H)-quinazolinone and a liquid vehicle about 50 percent to about 99 percent by weight of vegetable oil, contains a sweetening agent in a range of about 1.0 percent to about 50 percent by weight.

In a third embodiment, a capsule or compressed tablet pharmaceutical dosage form comprises:

(a) a therapeutically effective amount of the methanol solvate of (−)-6-Chloro-4-cyclopropylethynyl-4-trifluoromethyl-3,4-dihydro-2(1H)-quinazolinone;

(b) a surfactant;

(c) a disintegrant;

(d) a binder; and (e) a lubricant.

In a preferred embodiment, the therapeutically effective amount is about 50 mg to about 200 mg of the methanol solvate of (−)-6-Chloro-4-cyclopropylethynyl-4-trifluoromethyl-3,4-dihydro-2(1H)-quinazolinone, the surfactant is sodium lauryl sulfate, the disintegrant is sodium starch glycolate, the binder is lactose and the lubricant is magnesium stearate.

In a fourth embodiment, the present invention describes a method for inhibiting viral replication by a virally encoded reverse transcriptase which comprises providing the methanol solvate of (−)-6-Chloro-4-cyclopropylethynyl-4-trifluoromethyl-3,4-dihydro-2(1H)-quinazolinone, in an amount sufficient to result in the HIV reverse transcriptase being contacted with an effective inhibitory amount of the active drug substance.

In a preferred embodiment, the compound is provided to a human or animal subject to inhibit HIV reverse transcriptase in vivo.

In a fifth embodiment, the present invention describes a method for the treatment of human immunodeficiency virus infection which comprises administering to a host in need of such treatment a therapeutically effective amount of the methanol solvate of (−)-6-Chloro-4-cyclopropylethynyl-4-trifluoromethyl-3,4-dihydro-2(1H)-quinazolinone.

In a preferred embodiment, the methanol solvate of (−)-6-Chloro-4-cyclopropylethynyl-4-trifluoromethyl- 3,4-dihydro-2(1H)-quinazolinone is administered at a dosage from about 1 to about 1000 mg per dose.

In a more preferred embodiment, the methanol solvate of (−)-6-Chloro-4-cyclopropylethynyl-4-trifluoromethyl-3,4-dihydro-2(1H)-quinazolinone is administered at a dosage from about 50 mg to about 300 mg per dose.

In an even more preferred embodiment, the methanol solvate of (−)-6-Chloro-4-cyclopropylethynyl-4-trifluoromethyl-3,4-dihydro-2(1H)-quinazolinone is administered at a dosage from about 50 mg to about 200 mg per dose.

In a sixth embodiment, the methanol solvate of (−)-6-Chloro-4-cyclopropylethynyl-4-trifluoromethyl-3,4-dihydro-2(1H)-quinazolinone is prepared by recrystallization of (−)-6-Chloro-4-cyclopropylethynyl-4-trifluoromethyl-3,4-dihydro-2(1H)-quinazolinone from methanol.

In a seventh embodiment, the present invention provides Form 2 of crystalline (−)-6-Chloro-4-cyclopropylethynyl-4-trifluoromethyl-3,4-dihydro-2(1H)-quinazolinone.

In a preferred embodiment, Form 2 of (−)-6-Chloro-4-cyclopropylethynyl-4-trifluoromethyl-3,4-dihydro-2(1H)-quinazolinone is in substantially pure form.

In another preferred embodiment, Form 2 of (−)-6-Chloro-4-cyclopropylethynyl-4-trifluoromethyl-3,4-dihydro-2(1H)-quinazolinone is characterized by an x-ray powder diffraction pattern comprising three or more 2θ values selected from the group consisting of: 10.41±0.2, 11.25±0.2, 11.61±0.2, 19.46±0.2, 19.88±0.2, 22.17±0.2, 22.89±0.2, 25.57±0.2, and 26.38±0.2.

Figure 2:
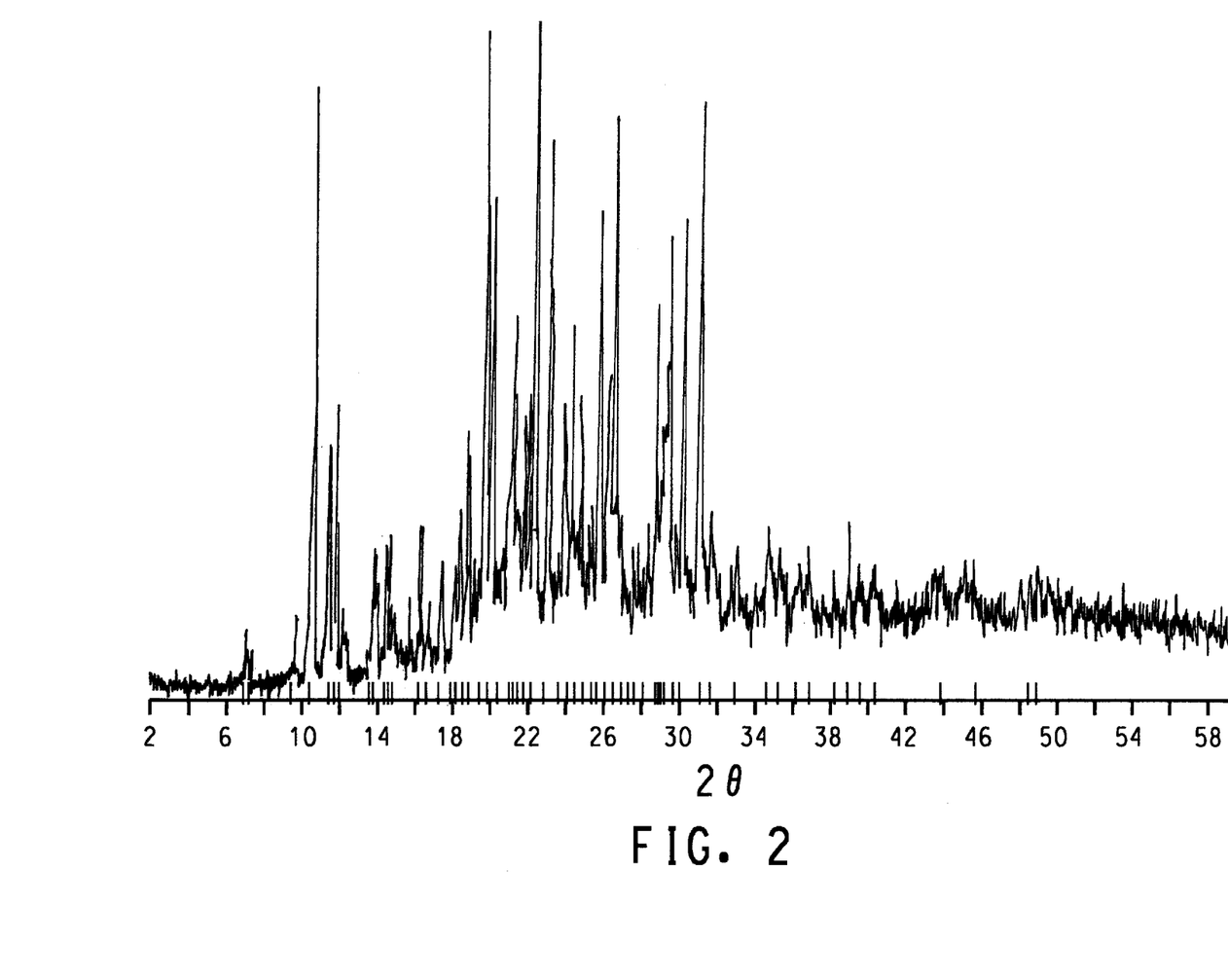
FIG. 2 shows a powder x-ray diffractogram of Form 2, the preferred crystalline form of (-)-6-Chloro-4-cyclopropylethynyl-4-trifluoromethyl-3,4-dihydro-2(1H)-quinazolinone.

In another preferred embodiment, Form 2 of (−)-6-Chloro-4-cyclopropylethynyl-4-trifluoromethyl-3,4-dihydro-2(1H)-quinazolinone is characterized by an x-ray powder diffraction pattern substantially in accordance with that shown in FIG. 2.

In another preferred embodiment, Form 2 of (−)-6-Chloro-4-cyclopropylethynyl-4-trifluoromethyl-3,4-dihydro-2(1H)-quinazolinone is characterized by a differential scanning calorimetry thermogram having a peak at about 183° C. to about 186° C.

In a more preferred embodiment, Form 2 of (−)-6-Chloro-4-cyclopropylethynyl-4-trifluoromethyl-3,4-dihydro-2(1H)-quinazolinone is characterized by an x-ray powder diffraction pattern comprising three or more 2θ values selected from the group consisting of: 10.41±0.2, 11.25±0.2, 11.61±0.2, 19.46±0.2, 19.88±0.2, 22.17±0.2, 22.89±0.2, 25.57±0.2, and 26.38±0.2, and further characterized by a differential scanning calorimetry thermogram having a peak at about 183° C. to about 186° C.

In an eigth embodiment, the present invention describes a pharmaceutical composition comprising a therapeutically effective amount of Form 2 of (−)-6-Chloro-4-cyclopropylethynyl-4-trifluoromethyl-3,4-dihydro-2(1H)-quinazolinone and a pharmaceutically acceptable carrier.

In a preferred embodiment, the pharmaceutical composition is contained in a capsule or compressed tablet dosage form, wherein the therapeutically effective amount is about 1 mg to about 1000 mg of Form 2 of (−)-6-Chloro-4-cyclopropylethynyl-4-trifluoromethyl-3,4-dihydro-2(1H)-quinazolinone.

In a more preferred embodiment, the pharmaceutical composition is contained in a capsule or compressed tablet dosage form, wherein the therapeutically effective amount is about 50 mg to about 300 mg of Form 2 of (−)-6-Chloro-4-cyclopropylethynyl-4-trifluoromethyl-3,4-dihydro-2(1H)-quinazolinone.

In an even more preferred embodiment, the pharmaceutical composition is contained in a capsule or compressed tablet dosage form, wherein the therapeutically effective amount is about 50 mg to about 200 mg of Form 2 of (−)-6-Chloro-4-cyclopropylethynyl-4-trifluoromethyl-3,4-dihydro-2(1H)-quinazolinone.

In another more preferred embodiment, the pharmaceutical composition contained in a capsule or compressed tablet contains greater than about 10% by weight of a disintegrant relative to the total dry weight of the dosage form.

In another preferred embodiment, the pharmaceutical composition is in liquid form.

In a more preferred embodiment, the liquid form comprises about 0.1 percent to about 15 percent by weight of Form 2 of (−)-6-Chloro-4-cyclopropyl-ethynyl-4-trifluoromethyl-3,4-dihydro-2(1H)-quinazolinone and a liquid vehicle comprising about 50 percent to about 99 percent by weight of polyolesters of medium chain fatty acids.

In an even more preferred embodiment, the composition is contained in a soft gelatin capsule, wherein the polyol esters of medium chain fatty acids consist essentially of $C_8$ to $C_{10}$ fatty acid triglycerides.

In another more preferred embodiment, the liquid form comprising about 0.1 percent to about 15 percent by weight of Form 2 of (−)-6-Chloro-4-cyclopropylethynyl-4-trifluoromethyl-3,4-dihydro-2(1H)-quinazolinone and a liquid vehicle comprising about 50 percent to about 99 percent by weight of polyolesters of medium chain fatty acids contains a sweetening agent in a range of about 0.1 percent to about 50 percent by weight.

In another more preferred embodiment, the pharmaceutical composition which is in liquid form comprises about 0.1 percent to about 10 percent by weight of Form 2 of (−)-6-Chloro-4-cyclopropylethynyl-4-trifluoromethyl-3,4-dihydro-2(1H)-quinazolinone and a liquid vehicle about 50 percent to about 99 percent by weight of vegetable oil.

In an even more preferred emobodiment, the pharmaceutical composition is contained in a soft gelatin capsule, wherein the vegatable oil is soybean oil or peanut oil.

In another more preferred embodiment, the pharmaceutical composition which is in liquid form comprising about 0.1 percent to about 10 percent by weight of Form 2 of (−)-6-Chloro-4-cyclopropylethynyl-4-trifluoromethyl-3,4-dihydro-2(1H)-quinazolinone and a liquid vehicle about 50 percent to about 99 percent by weight of vegetable oil, contains a sweetening agent in a range of about 1.0 percent to about 50 percent by weight.

In a ninth embodiment, a capsule or compressed tablet pharmaceutical dosage form comprises:

(a) a therapeutically effective amount of Form 2 of (−)-6-Chloro-4-cyclopropylethynyl-4-trifluoromethyl-3,4-dihydro-2(1H)-quinazolinone;

(b) a surfactant;

(c) a disintegrant;

(d) a binder; and (e) a lubricant.

In a preferred embodiment, the therapeutically effective amount is about 50 mg to about 200 mg of Form 2 of (−)-6-Chloro-4-cyclopropylethynyl-4-trifluoromethyl-3,4-dihydro-2(1H)-quinazolinone, the surfactant is sodium lauryl sulfate, the disintegrant is sodium starch glycolate, the binder is lactose and the lubricant is magnesium stearate.

In a tenth embodiment, the present invention describes a method for inhibiting viral replication by a virally encoded reverse transcriptase which comprises providing Form 2 of (−)-6-Chloro-4-cyclopropylethynyl-4-trifluoromethyl-3,4-dihydro-2(1H)-quinazolinone, in an amount sufficient to result in the HIV reverse transcriptase being contacted with an effective inhibitory amount of the active drug substance.

In a preferred embodiment, the compound is provided to a human or animal subject to inhibit HIV reverse transcriptase in vivo.

In an eleventh embodiment, the present invention describes a method for the treatment of human immunodeficiency virus infection which comprises administering to a host in need of such treatment a therapeutically effective amount of Form 2 of (−)-6-Chloro-4-cyclopropylethynyl-4-trifluoromethyl-3,4-dihydro-2(1H)-quinazolinone.

In a preferred embodiment, Form 2 of (−)-6-Chloro-4-cyclopropylethynyl-4-trifluoromethyl-3,4-dihydro-2(1H)-quinazolinone is administered at a dosage from about 1 to about 1000 mg per dose.

In a more preferred embodiment, Form 2 of (−)-6-Chloro-4-cyclopropylethynyl-4-trifluoromethyl-3,4-dihydro-2(1H)-quinazolinone is administered at a dosage from about 50 mg to about 300 mg per dose.

In an even more preferred embodiment, Form 2 of (−)-6-Chloro-4-cyclopropylethynyl-4-trifluoromethyl-3,4-dihydro-2(1H)-quinazolinone is administered at a dosage from about 50 mg to about 200 mg per dose.

In a twelfth embodiment, the present invention describes a method of treating HIV infection which comprises administering, in combination, to a host in need thereof a therapeutically effective amount of:
(a) Form 2 of (−)-6-Chloro-4-cyclopropylethynyl-4-trifluoromethyl-3,4-dihydro-2(1H)-quinazolinone; and
(b) at least one compound selected from the group consisting of HIV reverse transcriptase inhibitors and HIV protease inhibitors.

In a thirteenth embodiment, the present invention describes a pharmaceutical composition comprising a therapeutically effective amount of the methanol solvate of (−)-6-Chloro-4-cyclopropyl-ethynyl-4-trifluoromethyl-3,4-dihydro-2(1H)-quinazolinone, Form 2 of (−)-6-Chloro-4-cyclopropyl-ethynyl-4-trifluoromethyl-3,4-dihydro-2(1H)-quinazolinone, or mixtures thereof and a pharmaceutically acceptable carrier.

The potent reverse transcriptase inhibitor (−)-6-Chloro-4-cyclopropylethynyl-4-trifluoromethyl-3,4-dihydro-2(1H)-quinazolinone is represented by formula (I):

(I)

The two Forms of compound (I) described herein are distinguishable from one another by x-ray powder diffraction (XRD) and differential scanning calorimetry (DSC). Form 1 can be further identified by Nuclear Magnetic Resonance Spectroscopy (NMR), particularly with regard to the resonance of the methyl protons associated with the methanol of the solvate. Synthesis of (I) can be accomplished through a three-pot process from compound (II) as shown in Scheme 1.

-continued (VII) → formic acid → (I)

The preparation of compound (II) can be accomplished by methods well known to the skilled artisan of organic synthesis, and by methods taught in commonly assigned U.S. patent application Ser. No. 09/056,820, and *Tet. Lett.* 1994, 35(37), 6811–6814, the disclosures of which are hereby incorporated by reference. Dissolution of compound (II) in THF containing 5% v/v 1N HCl followed by treatment with about 2 equivalents of (R)-(+)-a-methylbenzyl isocyanate between 0° C. and ambient temperature effects condensation of the isocyanate with the aniline nitrogen of (II). The second equivalent of isocyanate is decomposed under the reaction conditions to give $CO_2$ and (R)-(+)-a-methyl-benzylamine hydrochloride salt. The urea condensation product reacts further to condense intramolecularly with the ketone to give the bicyclic urea hemiaminal (IV) as a mixture of diastereomers. The second condensation event takes place only slowly at ambient temperature. However, heating the reaction to reflux (65° C.) completes the conversion to (IV) within a couple of hours. The resulting mixture is washed with water to remove the benzylamine salt, and the THF is replaced with toluene via reduced pressure distillation (75 to 90° C. at 240 to 400 torr) crystallize the product. The mixture is cooled to 0° C., the product filtered, washed with toluene, and dried in an oven at 70° C. under 25 mm Hg vacuum for 15 to 20 hours until constant weight is achieved. Isolated yields are generally about 90%.

The hemiaminal (IV) is suspended in toluene and treated with five equivalents of triethylamine to create a homogeneous mixture. The mixture is cooled to 0° C. and treated with thionyl chloride in order to dehydrate both diastereomers of the hemiaminal (this generally takes one hour) to give a common intermediate. The resulting mixture is cooled to −50° C. and treated with three equivalents of lithiated cyclopropylacetylene (CPA-Li) or magnesium chloride cyclopropylacetylene (CPA-MgCl) in THF. The CPA-Li is generated by treating CPA in THF with n-hexyl or n-butyl lithium. The reaction is typically quenched with aqueous citric acid. After phase separation and concentration via distillation, most of the toluene is exchanged for methanol. The solvent exchange followed by cooling to 5° C. serves to crystallize a single diastereomer of (VII). The product is filtered and washed with cold methanol, prior to drying at 40° C. under 25 mm Hg vacuum. Isolated yields of (VII) are routinely around 80%.

Compound (VII) is debenzylated in about two volumes w/v of trifluoroacetic acid (TFA) in the presence of 5% water (based on the volume of acid) at ambient temperature in about an hour. Five volumes of toluene is added to the reaction, and the resulting mixture is cooled to 0° C. 10N NaOH is added to the reaction mixture maintaining the temperature below 20° C. to neutralize the TFA. After phase separation and concentration via distillation, heptanes are added to the reaction mixture at roughly 90° C. The concentration and heptane addition causes the final product (I) to crystallize. Cooling to 0° C. causes further crystallization. Filtration of the reaction mixture and washing with heptanes, followed by drying to a constant weight at 90° C. under 25 mm Hg vacuum, gives roughly an 85% isolated yield of compound (I).

The methanol solvate of (I) (Form 1) and the preferred crystalline form of (I) (Form 2) may be prepared by methods described in Scheme 2.

Scheme 2

Formation of Form 1

The methanol solvate of (−)-6-Chloro-4-cyclopropylethynyl-4-trifluoromethyl-3,4-dihydro-2(1H)-quinazolinone (Form 1) may be obtained directly from the quinazoline of formula (VII). Preferably, a strong acid is charged to a reaction vessel containing (VII). While numerous strong acids may be used, those with a pKa of <4.7 are preferred. Examples of such preferred acids include hydrochloric acid, nitric acid, sulfuric acid, phosphoric acid, formic acid, trifluoroacetic acid and methane sulfonic acid. Trifluoroacetic acid and formic acid are more preferred. Formic acid is most preferred. In addition to the use of strong acids to affect ionization, additional acids such as sulfonic based acids and carboxylic acids can be added to act as the solvent and/or solvolysis agent. The volume of acid is typically based on the weight of compound (VII), and is preferably about 1 mL per gram to about 10 mL per gram. More preferred is about 3 mL per gram to about 7 mL per gram. An additional solvent may also be added to enhance the rate of ionization. Preferred solvents for this purpose include water, methanol, ethanol, isopropanol, dichloromethane, chloroform, thioanisole, chlorobutane, toluene, heptane, anisole, thiophenol, triethylsilane, and poly(methyl-hydrosilane). Water is the most preferred solvent for this purpose.

The reaction may be carried out at temperatures in the range of about −20° C. to about 150° C. The preferred temperature range is about 20° C. to about 100° C. More preferred is about 50° C. to about 70° C. At suitable temperatures, the reaction is usually complete after about 0.25 hours to about 20 hours. The preferred temperatures typically provide the product after about 1 to about 2 hours. Reaction completion is preferably determined by HPLC. Under preferred conditions, the conversion of (VII) to (I) is >99% by area at completion (or <1% starting material).

The acid is preferably removed by extraction of the reaction mixture with water. The reaction mixture is preferably diluted by the addition of water and an additional solvent suitable for work-up may be added. The choice of solvent and amount will be readily understood by one skilled in the art. By way of example, water may be added in an amount in the range of about 1 mL per gram (VII) to about 10 mL per gram (VII). More preferred is about 3 mL per gram to about 7 mL per gram.

As mentioned, an additional solvent may be added to assist in the extraction. Preferred solvents for this purpose include toluene, heptane, hexane, pentane, methyl acetate, ethyl acetate, chloroform, methylene chloride, chlorobutane and xylenes. The most preferred solvent is toluene, which has been found to solubilize various reaction impurities. The preferred amount of toluene is about 1 mL per gram (VII) to about 10 mL per gram (VII). More preferred is about 3 mL per gram to about 7 mL per gram.

The aqueous and organic phases are preferably contacted by stirring the mixture vigorously. The pH of the aqueous phase may be monitored to assure adequate removal of acid. Preferably, the pH of the mixture is about 2 or less. The aqueous phase may be drained and replaced with fresh water and the extraction procedure repeated until the desired pH is obtained.

The product may be precipitated by concentrating the organic phase, preferably by distillation. In order to afford Form 1, the methanolic solvate of (I), methanol is added. It will be well understood by one skilled in the art that additional solvates may be obtained by the addition of the appropriate solvent. Other solvates include, but are not limited to, acetates and those derived from homologous alcohols such as the ethanol solvate, the propanol solvate, the isopropyl solvate and the like. Addition of the solvent is preferably accompanied by continued removal of solvent by distillation until <5% of the solvent added for the work-up remains, as evidenced by GC analysis. The mixture is preferably cooled to afford a slurry.

The final product is isolated, preferably by filtration of the slurry, and washed with additional solvent. Preferred solvents for washing include methanol, heptanes, hexanes, and pentane. Most preferred is heptane.

Alternatively, Form 1 may be formed by recrystallizing crude (−)-6-Chloro-4-cyclopropylethynyl-4-trifluoromethyl-3,4-dihydro-2(1H)-quinazolinone from methanol. Procedures for recrystallization will be readily understood by one skilled in the art. By way of general guidance, the compound may be suspended and stirred in methanol. A slurry is an example of the compound suspended in methanol. The preferred amount of methanol for this purpose is about 1 mL per gram (I) to about 10 mL per gram (I). More preferred is about 2 mL per gram to about 4 mL per gram. The mixture may be heated for more effective conversion to Form 1. Preferred temperatures for this purpose are in the range of 30° C. to the refluxing temperature of solvent. More preferred is 60° C. to refluxing temperature of the solvent. By way of example, heating (I) in about 2.5 mL per gram of methanol at 65° C. affords Form 1 in about 1 hour. The mixture may be cooled to about −20° C. to about 0° C., filtered under vacuum and washed with a hydrocarbon solvent to afford Form 1.

Formation of Form 2

Transformation of Form 1 into Form 2 requires a thermal polymorphic conversion of the methanol solvate to the preferred crystalline form. Form 1 is preferably dried under vacuum at about 60° C. to about 130° C. in order to drive the methanol from the solids. More preferably, the solids are heated in a two step process: a first step to remove the methanol, followed by a second step to effect a polymorphic conversion from a metastable phase to Form 2. In the two step process the solids are first heated to about 85° C. to about 100° C., more preferably to about 90° C., and held at that temperature for about 1 to about 3 hours; followed by heating at about 115° C. to about 130° C., more preferably about 120° C. to about 125° C., for an additional about 1 to about 3 hours. By way of example, the methanol solvate generally undergoes a polymorphic conversion at about 90° C. under 25 mm Hg vacuum. The solids may be monitored by DSC and XRD to assure formation of the thermodynamic polymorph of the product. The resulting thermodynamic polymorph is typically produced in roughly 93% isolated yield. Form 2 is preferably comilled or passed through a 14 mesh screen to delump the product.

Differential Scanning Calorimetry (DSC) Analysis

Form 1, the methanol solvate, exhibits a broad endothermic transition in the range of about 90° C. to about 110° C., with a peak at about 109° C. to about 110° C., corresponding to the loss of methanol. An exothermic recrystallization transition immediately following the endotherm at about 110° C. may or may not be observed. This transition may be masked by the endotherm such that the endotherm appears to be split into two endotherms. Finally, a melt endotherm will follow in the temperature range of about 183° C. to about 186° C. representing Form 2.

The DSC of the high melting crystalline Form 2 demonstrates a characteristic single melt endotherm in the temperature range of about 183° C. to about 186° C.

X-Ray Diffraction (XRD) Analysis

All 2θ values have a standard deviation of ±0.2 unless otherwise indicated.

Form 1, the methanol solvate, has characteristic reflections with 2θ values of 9.26, 12.01, 15.02, 23.52, 24.08. In particular, peaks at 9.26 and 15.02 do not appear to overlap with any peaks seen in the Form 2 XRD pattern.

Form 2 has characteristic reflections with 2θ values of 19.46, 19.88, 22.17, 22.89, 25.57, and 26.38 degree 2θ. While these peaks are typical reflection for Form 2, it may be more difficult to use these values to differentiate Form 1 from Form 2 due to peak overlap. Generally, three prominent peaks in the 10–12 degree 2θ region may be used to distinguish the methanol solvate from Form 2. These three peaks have 2θ values of 10.408, 11.246, and 11.608.

Nuclear Magnetic Resonance Spectroscopy (NMR)

Form 1, the methanol solvate, has been characterized and distinguished from Form 2 by NMR. Specifically, the methyl protons of the methanol of the solvate appear as a singlet at about 3.49 ppm with a standard deviation of ±0.05 unless otherwise specified. Additional proton environments consistent with the methanol solvate of the compound of formula (I) have chemical shift values in the range of about 0.75 ppm to about 0.87 ppm; in the range of about 1.23 ppm to about 1.32 ppm; at about 1.82; in the range of about 6.78 ppm to about 6.80 ppm; in the range of about 7.22 to about 7.26; at about 7.48; and at about 9.67 ppm.

DEFINITIONS

The following abbreviations are used herein: "THF" is intended to mean tetrahydrofuran, "PCT" as used herein means process control test, "GC" as used herein is intended to mean gas chromatography, "HPLC" is intended to mean high performance liquid chromatography, "DMSO" is intended to mean dimethylsulfoxide, "TEA" is intended to mean triethylamine.

The reactions of the synthetic methods described herein are carried out in suitable solvents which may be readily selected by one of skill in the art of organic synthesis, said suitable solvents generally being any solvent which is substantially nonreactive with the starting materials (reactants), the intermediates, or products at the temperatures at which the reactions are carried out, i.e., temperatures which may range from the solvent's freezing temperature to the solvent's boiling temperature. A given reaction may be carried out in one solvent or a mixture of more than one solvent. Depending on the particular reaction, suitable solvents for a particular reaction or work-up following the reaction may be selected. Such suitable solvents, as used herein may include, by way of example and without limitation, chlorinated solvents, hydrocarbon solvents, ether solvents, polar protic solvents and polar aprotic solvents.

Suitable halogenated solvents include, but are not limited to carbon tetrachloride, bromodichloromethane, dibromochloromethane, bromoform, chloroform, bromochloromethane, dibromomethane, butyl chloride, dichloromethane, tetrachloroethylene, trichloroethylene, 1,1,1-trichloroethane, 1,1,2-trichloroethane, 1,1-dichloroethane, 2-chloropropane, hexafluorobenzene, 1,2,4-trichlorobenzene, o-dichlorobenzene, chlorobenzene, fluorobenzene, fluorotrichloromethane, chlorotrifluoromethane, bromotrifluoromethane, carbon tetrafluoride, dichlorofluoromethane, chlorodifluoromethane, trifluoromethane, 1,2-dichlorotetrafluorethane and hexafluoroethane.

Suitable hydrocarbon solvents include, but are not limited to benzene, cyclohexane, pentane, hexane, toluene, cycloheptane, methylcyclohexane, heptane, ethylbenzene, m-, o-, or p-xylene, octane, indane, nonane.

Suitable ether solvents include, but are not limited to dimethoxymethane, tetrahydrofuran, 1,3-dioxane, 1,4-dioxane, furan, diethyl ether, ethylene glycol dimethyl ether, ethylene glycol diethyl ether, diethylene glycol dimethyl ether, diethylene glycol diethyl ether, triethylene glycol diisopropyl ether, anisole, or t-butyl methyl ether.

Suitable polar protic solvents include, but are not limited to methanol, ethanol, 2-nitroethanol, 2-fluoroethanol, 2,2,2-trifluoroethanol, ethylene glycol, 1-propanol, 2-propanol, 2-methoxyethanol, 1-butanol, 2-butanol, i-butyl alcohol, t-butyl alcohol, 2-ethoxyethanol, diethylene glycol, 1-, 2-, or 3-pentanol, neo-pentyl alcohol, t-pentyl alcohol, diethylene glycol monomethyl ether, diethylene glycol monoethyl ether, cyclohexanol, benzyl alcohol, phenol, and glycerol.

Suitable polar aprotic solvents include, but are not limited to dimethylformamide (DMF), dimethylacetamide (DMAC), 1,3-dimethyl-3,4,5,6-tetrahydro-2(1H)-pyrimidinone (DMPU), 1,3-dimethyl-2-imidazolidinone (DMI), N-methylpyrrolidinone (NMP), formamide, N-methylacetamide, N-methylformamide, acetonitrile (ACN), dimethylsulfoxide, propionitrile, ethyl formate, methyl acetate, hexachloroacetone, acetone, ethyl methyl ketone, ethyl acetate, isopropyl acetate, t-butyl acetate, sulfolane, N,N-dimethylpropionamide, nitromethane, nitrobenzene, hexamethylphosphoramide.

As used herein, "strong acid" refers to any acid having a pKa less than 4.7. These include, but are not limited to mineral acids such as hydrochloric acid, hydrobromic acid, sulfuric acid, nitric acid, phosphoric acid; and organic acids such as formic acid, acetic acid, trifluoroacetic acid, ethanoic acid, propionic acid, butyric acid, valeric acid and caproic acid.

The present invention describes the methanol solvate of (I) (Form 1), and the preferred crystalline form of (I) (Form 2) in substantially pure form. As used herein, "substantially pure" means a compound having a purity greater than 90 percent, including 90, 91, 92, 93, 94, 95, 96, 97, 98, 99, and 100 percent.

When dissolved, (I) loses its crystalline structure, and is therefore is considered to be a solution of (I). All forms of the present invention, however, may be used for the preparation of liquid formulations in which the drug is dissolved or suspended. In addition, the crystalline or solvate forms of (I) may be incorporated into solid formulations.

The term "slurry" as used herein is intended to mean a saturated solution of (I) and an additional amount of (I) to give a heterogeneous solution of (I) and a solvent.

A therapeutically effective amount of the solvate or crystalline (I) is combined with a pharmaceutically acceptable carrier to produce the pharmaceutical compositions of this invention. By "therapeutically effective amount" it is meant an amount that, when administered alone or with an additional therapeutic agent, is effective to prevent, supress or ameliorate the disease or condition or the progression of the disease or condition. The combination of compounds described herein is preferably a synergistic combination. Synergy, as described for example by Chou and Talalay, Adv. Enzyme Regul. 22:27 . 55 (1984), occurs when the effect (in this case, inhibition of HIV replication) of the compounds when administered in combination is greater than the additive effect of the compounds when administered alone as a single agent. In general, a synergistic effect is most clearly demonstrated at suboptimal concentrations of the compounds. Synergy can be in terms of lower cytotoxicity, increased antiviral effect, or some other beneficial effect of the combination compared with the individual components.

The compounds of the present invention are useful in the inhibition of HIV reverse transcriptase, treatment of infection by human immunodeficiency virus (HIV) and the treatment of consequent pathological conditions such as acquired immunodeficiency syndrome (AIDS). Treating AIDS, or treating infection by HIV is defined as including, but not limited to, treatment and prevention of a wide range of states of HIV infection: AIDS, ARC (AIDS related complex), both symptomatic and asymptomatic, and actual or potential exposure to HIV by blood transfusion, exchange of bodily fluids, bites, accidental needle stick, or exposure to blood during surgery.

For these purposes, the compounds of the present invention may be administered orally, parenterally (including subcutaneous injections, intraveneous, intramuscular, intrasternal injection or infusion techniques), by inhalation spray, rectally, in dosage unit formulations containing conventional non-toxic pharmaceutically acceptable adjuvants and vehicles, all using dosage forms well known to those of ordinary skill in the pharmaceutical arts.

The crystalline and solvate forms of (I) described herein may be formulated into pharmaceutical compositions and employed in therapeutic and prophylactic methods as described in U.S. Pat. No. 5,519,021, which is hereby incorporated by reference. These methods include the direction of the forms of the present invention to combinations with one or more agents useful in the treatment of AIDS such as other HIV reverse transcriptase inhibitors, HIV protease inhibitors, antivirals, immunomodulators, antibiotics antiinfectives, or vaccines.

As used herein, "HIV reverse transcriptase inhibitor" is intended to refer to both nucleoside and non-nucleoside inhibitors of HIV reverse transcriptase (RT). Examples of nucleoside RT inhibitors include, but are not limited to, AZT, ddC, ddI, d4T, and 3TC. Examples of non-nucleoside RT inhibitors include, but are no limited to, delavirdine (Pharmacia and Upjohn U90152S), nevirapine (Boehringer Ingelheim), Ro 18,893 (Roche), trovirdine (Lilly), MKC-442 (Triangle), HBY 097 (Hoechst), ACT (Korean Research Institute), UC-781 (Rega Institute), UC-782 (Rega Institute), RD4-2025 (Tosoh Co. Ltd.), and MEN 10979 (Menarini Farmaceutici).

As used herein, "HIV protease inhibitor" is intended to refer to compounds which inhibit HIV protease. Examples include, but are not limited, saquinavir (Roche, Ro31-8959), ritonavir (Abbott, ABT-538), indinavir (Merck, MK-639), amprenavir (Vertex/Glaxo Wellcome), nelfinavir (Agouron, AG-1343), palinavir (Boehringer Ingelheim), BMS-232623 (Bristol-Myers Squibb), GS3333 (Gilead Sciences), KNI-413 (Japan Energy), KNI-272 (Japan Energy), LG-71350 (LG Chemical), CGP-61755 (Ciba-Geigy), PD 173606 (Parke Davis), PD 177298 (Parke Davis), PD 178390 (Parke Davis), PD 178392 (Parke Davis), U-140690 (Pharmacia and Upjohn), and ABT-378. Additional examples include the cyclic protease inhibitors disclosed in WO93/07128, WO94/19329, WO94/22840, and PCT Application Number US96/03426.

The crystalline and solvate forms of (I) of this invention may be administered in oral dosage forms such as tablets, capsules (each of which includes sustained release or timed release formulations), pills, powders, granules, elixirs, tinctures, suspensions, syrups, and emulsions.

Solid dosage forms (pharmaceutical compositions) suitable for administration may generally contain from about 1 mg to about 1000 mg of the solvate or crystalline (I) per dosage unit.

For oral administration in solid form such as a tablet or capsule, the solvate or crystalline (I) can be combined with a non-toxic, pharmaceutically acceptable inert carrier, such as lactose, starch, sucrose, glucose, methylcellulose, magnesium stearate, dicalcium phosphate, calcium sulfate, mannitol, sorbitol and the like.

Preferably, in addition to the active ingredient, solid dosage forms contain a number of additional ingredients referred to herein as "excipients". These excipients include among others diluents, binders, lubricants, glidants and disintegrants. Coloring agents may also be incorporated. "Diluents" as used herein, are agents which impart bulk to the formulation to make a tablet a practical size for compression. Examples of diluents are lactose and cellulose. "Binders" as used herein, are agents used to impart cohesive qualities to the powered material ensuring the tablet will remain intact after compression, as well as improving the free-flowing qualities of the powder. Examples of typical binders are lactose, starch and various sugars. "Lubricants" as used herein have several functions including preventing the adhesion of the tablets to the compression equipment and improving the flow of the granulation prior to compression or encapsulation. Lubricants are in most cases hydrophobic materials. Excessive use of lubricants can result in a formulation with reduced disintegration and/or delayed dissolution of the drug substance. "Glidants" as used herein are substances which improve the flow characteristics of the granulation material. Examples of glidants include talc and colloidal silicon dioxide. "Disintegrants" as used herein are substances or a mixture of substances added to a formulation to facilitate the breakup or disintegration of the solid dosage form after administration. Materials that serve as disintegrants include starches, clays, celluloses, algins, gums and cross-linked polymers. A group of disintegrants referred to as "super-disintegrants" generally are used at a low level in the solid dosage form, typically 1% to 10% by weight relative to the total weight of the dosage unit. Croscarmelose, crospovidone and sodium starch glycolate represent examples of a cross-linked cellulose, a cross-linked polymer and a cross-linked starch, respectively. Sodium starch glycolate swells seven- to twelve-fold in less than 30 seconds effectively disintegrating the granulations that contain it.

The disintegrant preferably used in the present invention is selected from the group comprising modified starches, croscarmallose sodium, carboxymethylcellulose calcium and crospovidone. A more preferred disintegrant in the present invention is a modified starch such as sodium starch glycolate.

Preferred carriers include capsules or compressed tablets which contain the solid pharmaceutical dosage forms described herein. Preferred capsule or compressed tablet forms generally comprise a therapeutically effective amount of the solvate or crystalline (I) and one or more disintegrants in an amount greater than about 10% by weight relative to the total weight of the contents of the capsule or the total weight of the tablet.

Preferred capsule formulations may contain the solvate or crystalline (I) present in an amount from about 5 to about 1000 mg per capsule. Preferred compressed tablet formulations contain (I) in an amount from about 5 mg to about 800 mg per tablet. More preferred formulations contain about 50 to about 300 mg per capsule or compressed tablet. Even more preferred formulations contain about 50 to about 200 mg per capsule or compressed tablet. Preferably, the capsule or compressed tablet pharmaceutical dosage form comprises a therapeutically effective amount of Form 1, or Form 2; a surfactant; a disintegrant; a binder; a lubricant; and optionally additional pharmaceutically acceptable excipients such as diluents, glidants and the like; wherein the disintegrant is selected from modified starches; croscarmallose sodium, carboxymethylcellulose calcium and crospovidone.

In general, liquid pharmaceutical compositions for oral administration have ranges of the HIV reverse transcriptase inhibitor agents which can vary from about 0.1 to about 15% by weight (wgt). More preferably, the drug substance component will range from about 1 to about 10% by weight in the composition.

For oral administration in liquid form, the solvate or crystalline (I) can be combined with any oral, non-toxic pharmaceutically acceptable inert carrier such as ethanol, glycerol, water and the like. In a preferred liquid composition, the liquid vehicle consists of essentially polyol esters of medium chain fatty acids. This term polyol esters of medium chain fatty acids is intended to include esters and mixed esters of glycerol, propylene glycol or other open chain polyols such as polyethylene glycol, reacted with medium chain fatty acids, wherein said acid has a chain length between 6 and 12 carbon atoms. Particularly preferred for compositions are triglycerides or diglycerides of the $C_8$–$C_{10}$ fatty acids commercially available from the fractionation of coconut oil. Commercially available products of this description are sold under the trade names "Miglyol" and "Captex 300" which are described as having a typical composition of about 68% $C_8$ fatty acid (caprylic) triglyceride and about 28% $C_{10}$ fatty acid (capric) triglyceride with minor levels of $C_6$ and $C_{14}$ fatty acid triglycerides.

The medium chain fatty acid ester component, when present serves as the solvent vehicle for the active agent in formulating the compositions of the invention and is present in the composition in the range from about 50% to about 99%, by weight, but more preferably from 70% to 99% by weight.

Preferably, the liquid composition containing polyol esters will contain a sweetening agent which is useful in reducing the oily taste of the medium chain fatty acid ester and thus contributes in a significant way in making the compositions more palatable.

The sweetening agent can be selected from a sugar such as sucrose, mannitol, sorbitol, xylitol, lactose, etc. or a sugar substitute such as cyclamate, saccaharin, aspartame, etc. If sugar substitutes are selected as the sweetening agent the amount employed in the compositions of the invention will be substantially less than if sugars are employed. Taking this into account, the sweetening agent can be used in the composition in the range of from 0.1 to 50% by weight and more preferably in the range of 0.5 to 30% by weight.

The more preferred sweetening agents are the sugars and particularly sucrose. The particle size of the powdered sucrose used has been found to have a significant influence in the physical appearance of the finished composition and its ultimate acceptance for taste. The preferred particle size of the sucrose component when used is in the range of from 200 to less than 325 mesh US Standard Screen.

In another preferable liquid pharmaceutical composition, the solvate or crystalline (I) is combined with a liquid vehicle which is a vegetable oil selected from the class consisting of olive oil, peanut oil, soybean oil, corn oil, safflower oil, sunflower oil, canola oil, or walnut oil. These vegetable oils are commercially available from a number of sources well recognized by those skilled in the art.

The vegetable oil component serves as the solvent vehicle for the active agent in formulating the compositions of the invention and is present in the composition in the range from 50 to 99%, by weight more preferably from 70% to 99% by weight.

Preferably, the pharmaceutical compositions containing vegetable oil will also contain a sweetening agent which is useful in reducing the oily taste of the vegetable oil and thus contributes in a significant way in making the compositions more palatable.

The liquid compositions may also contain other components routinely utilized in formulating pharmaceutical compositions. One example of such components is lecithin. Its use in compositions of the invention as an emulsifying agent in the range of from 0.05 to 1% by weight, more preferably from 0.1 to 0.5% by weight may possibly serve to improve absorption of the active drug agent. Other examples of components that may be used are antimicrobial preservatives, such as benzoic acid or parabens; suspending agents, such as colloidal silicon dioxide; antioxidants; topical oral anesthetics; flavoring agents; and colorants.

The selection of such optional components and their level of use in the compositions of the invention is within the level of skill in the art and will be even better appreciated from the working examples provided hereinafter.

The solvate or crystalline (I) may also be coupled with soluble polymers as targetable drug carriers. Such polymers can include polyvinylpyrrolidine pyran copolymer, polyhydroxypropylmethacrylamide-phenol, polyhydroxyethylaspartamidephenol or polyethylene oxide-polylysine substituted with palmitolyl residues. Furthermore, the crystalline (I) may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and crosslinked or amphipathic block copolymers of hydrogels.

Gelatin capsules of the solvate or crystalline (I) contain the solvate or crystalline (I) and the liquid or solid compositions described herein. Gelatin capsules may also contain powdered carriers such as lactose, starch, cellulose derivatives, magnesium stearate, stearic acid and the like. Similar diluents can be used to make compressed tablets. Both tablets and capsules can be manufactured as sustained release products to provide for continuous release of medication over a period of hours. Tablets can be sugar coated or film coated to mask any unpleasant taste and to protect the tablet from the atmosphere or enteric coated for selective disintegration in the gastrointestinal track.

In general, water, a suitable oil, saline, aqueous dextrose (glucose), and related sugar solutions and glycols, such as propylene glycol or polyethylene glycols are suitable carriers for parenteral solutions. Solutions for parenteral solutions are prepared by dissolving the solvate or crystalline (I) in the carrier and, if necessary, adding buffering substances. Anti-oxidizing agents such as sodium bisulfite, sodium sulfite, or ascorbic acid either alone or combined, are suitable stabilizing agents. Citric acid and its salts and sodium EDTA may also be employed. Parenteral solutions may also contain preservatives, such as benzalkonium chluoride, methyl- or propyl-paraben and chlorobutanol.

Suitable pharmaceutical carriers are described in Remington's Pharmaceutical Sciences, Mack Publishing Co., a standard reference text in this field. Useful pharmaceutical dosage-forms for administration of the compounds of this invention can be illustrated as follows:

Capsules

A large number of unit capsules can be prepared by filling standard two-piece hard gelatin capsules each with 100 mg of powdered active ingredient, 150 mg of lactose, 50 mg of cellulose, and 6 mg magnesium stearic.

Soft Gelatin Capsules

A mixture of active ingredient in a digestible oil such as soybean oil, cottonseed oil or olive oil can be prepared and injected by means of a positive displacement pump into gelatin to form soft gelatin capsules containing 100 mg of the active ingredient. The capsules should then be washed and dried.

Tablets

A large number of tablets can be prepared by conventional procedures so that the dosage unit is 100 mg of active ingredient, 0.2 mg of colloidal silicon dioxide, 5 milligrams of magnesium stearate, 275 mg of microcrystalline cellulose, 11 mg of starch and 98.8 mg of lactose. Appropriate coatings may be applied to increase palatability or delay absorption.

Suspension

An aqueous suspension can be prepared for oral administration so that each 5 mL contain 25 mg of finely divided active ingredient, 200 mg of sodium carboxymethyl cellulose, 5 mg of sodium benzoate, 1.0 g of sorbitol solution, U.S.P., and 0.025 mg of vanillin.

Injectable

A parenteral composition suitable for administration by injection can be prepared by stirring 1.5% by weight of active ingredient in 10% by volume propylene glycol and water. The solution is sterilized by commonly used techniques.

Nasal Spray

An aqueous solution is prepared such that each 1 milliliter contains 10 milligrams of active ingredient, 1.8 milligrams methylparaben, 0.2 milligram propylparaben and 10 milligrams methylcellulose. The solution is dispensed into 1 milliliter vials.

Lung Inhaler

A homogeneous mixture of the active ingredient in polysorbate 80 is prepared such that the final concentration of the active ingredient will be 10 milligrams per container and the final concentration of polysorbate 80 in the container will be 1% by weight. The mixture is dispensed into each can, the valves are crimped onto the can and the required amount of dichlorotetrafluoroethane is added under pressure.

Combination of Components (a) and (b)

The Form 1 or Form 2 therapeutic agent component (a) of this invention can independently be in any dosage form, such as those described above, and can also be administered in various combinations, as described above. In the following description component (b) is to be understood to represent one or more agents as described previously. Thus, if components (a) and (b) are to be treated the same or independently, each agent of component (b) may also be treated the same or independently.

Components (a) and (b) of the present invention may be formulated together, in a single dosage unit (that is, combined together in one capsule, tablet, powder, or liquid, etc.) as a combination product. When component (a) and (b) are not formulated together in a single dosage unit, the component (a) may be administered at the same time as component (b) or in any order; for example component (a) of this invention may be administered first, followed by administration of component (b), or they may be administered in the revserse order. If component (b) contains more that one agent, e.g., one RT inhibitor and one protease inhibitor, these agents may be administered together or in any order. When not administered at the same time, preferably the administration of component (a) and (b) occurs less than about one hour apart. Preferably, the route of administration of component (a) and (b) is oral. The terms oral agent, oral inhibitor, oral compound, or the like, as used herein, denote compounds which may be orally administered. Although it is preferable that component (a) and component (b) both be administered by the same route (that is, for example, both orally) or dosage form, if desired, they may each be administered by different routes (that is, for example, one component of the combination product may be administered orally, and another component may be administered intravenously) or dosage forms.

As is appreciated by a medical practitioner skilled in the art, the dosage of the combination therapy of the invention may vary depending upon various factors such as the pharmacodynamic characteristics of the particular agent and its mode and route of administration, the age, health and weight of the recipient, the nature and extent of the symptoms, the kind of concurrent treatment, the frequency of treatment, and the effect desired, as described above.

The proper dosage of components (a) and (b) of the present invention will be readily ascertainable by a medical practitioner skilled in the art, based upon the present disclosure. By way of general guidance, typically a daily dosage may be about 100 milligrams to about 1.5 grams of each component. If component (b) represents more than one compound, then typically a daily dosage may be about 100 milligrams to about 1.5 grams of each agent of component (b). By way of general guidance, when the compounds of component (a) and component (b) are administered in combination, the dosage amount of each component may be reduced by about 70–80% relative to the usual dosage of the component when it is administered alone as a single agent for the treatment of HIV infection, in view of the synergistic effect of the combination.

The combination products of this invention may be formulated such that, although the active ingredients are combined in a single dosage unit, the physical contact between the active ingredients is minimized. In order to minimize contact, for example, where the product is orally administered, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. Another embodiment of this invention where oral administration is desired provides for a combination product wherein one of the active ingredients is coated with a sustained-release material which effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low-viscosity grade of hydroxypropyl methylcellulose or other appropriate materials as known in the art, in order to further separate the active components. The polymer coating serves to form an additional barrier to interaction with the other component. In each formulation wherein contact is prevented between components (a) and (b) via a coating or some other material, contact may also be prevented between the individual agents of component (b).

Dosage forms of the combination products of the present invention wherein one active ingredient is enteric coated can be in the form of tablets such that the enteric coated component and the other active ingredient are blended together and then compressed into a tablet or such that the enteric coated component is compressed into one tablet layer and the other active ingredient is compressed into an additional layer. Optionally, in order to further separate the two layers, one or more placebo layers may be present such that the placebo layer is between the layers of active ingredients. In addition, dosage forms of the present invention can be in the form of capsules wherein one active ingredient is compressed into a tablet or in the form of a plurality of microtablets, particles, granules or non-perils, which are then enteric coated. These enteric coated microtablets, particles, granules or non-perils are then placed into a capsule or compressed into a capsule along with a granulation of the other active ingredient.

These as well as other ways of minimizing contact between the components of combination products of the present invention, whether administered in a single dosage form or administered in separate forms but at the same time or concurrently by the same manner, will be readily apparent to those skilled in the art, based on the present disclosure.

Pharmaceutical kits useful for the treatment of HIV infection, which comprise a therapeutically effective amount of a pharmaceutical composition comprising a compound of component (a) and one or more compounds of component (b), in one or more sterile containers, are also within the ambit of the present invention. Sterilization of the container may be carried out using conventional sterilization methodology well known to those skilled in the art. Component (a) and component (b) may be in the same sterile container or in separate sterile containers. The sterile containers of materials may comprise separate containers, or one or more multi-part containers, as desired. Component (a) and component (b), may be separate, or physically combined into a single dosage form or unit as described above. Such kits may further include, if desired, one or more of various conventional pharmaceutical kit components, such as for example, one or more pharmaceutically acceptable carriers, additional vials for mixing the components, etc., as will be readily apparent to those skilled in the art. Instructions, either as inserts or as labels, indicating quantities of the components to be administered, guidelines for administration, and/or guidelines for mixing the components, may also be included in the kit.

Obviously, numerous modifications and variations of the present invention are possible in light of the above teachings. It is therefore to be understood that within the scope of the appended claims, the invention may be practiced otherwise than as specifically described herein.

The following exemplify the synthetic preparation of crude (−)-6-Chloro-4-cyclopropyl-ethynyl-4-trifluoromethyl-3,4-dihydro-2(1H)-quinazolinone.

EXAMPLE 1

Preparation of Quinazolone (IV) from Ketone (II)

A 100 gallon reactor was charged with solid (II) as its hydrochloride hydrate (21 kg, 75.51 moles) followed by THF (93 kg), water (7 kg), and 37% HCl (0.72 kg). The mixture was stirred until homogeneous at ambient temperature (0.5 h) and cooled to between 0 and 5° C. Neat (R)-(+)-a-methylbenzyl isocyanate (22.2 kg, 150.83 moles) was added to the reaction mixture over 1 to 2 hours while maintaining an internal temperature of 0 to 5° C. throughout the addition. Immediately after the isocyanate addition, the jacket temperature was increased to roughly 10 to 15° C. for 3 hours (mild gas evolution was constant). The jacket temperature was increased to roughly 15° C. and held for 15 to 20 hours. Intermediate conversion checks (A % by HPLC) are made based on consumption of isocyanate. After complete isocyanate consumption (<1 A % at 215 nm by HPLC), the temperature is increased to between 60 to 65° C. for about 2 hours, until acyclic urea (II-a) is no longer detected by HPLC. The reaction is cooled to about 20° C.

PCT (process control test): A sample was taken from the vessel to obtain in-process information. The weight percent of (II) and (IV) is determined by HPLC. When conversion was deemed sufficient, the reaction was quenched.

Water (53 L) was added to the reaction mixture followed by toluene (36 kg), and the mixture was stirred for 0.5 hours. After holding for 0.5 hours, the phases were separated. The organic layer was washed with water (53 L) (mix for 0.5 h, let sit about 0.5 h), and the phases separated.

Toluene (55 kg) was added to the organic phase at roughly 20° C. The solvent distilled off under reduced pressure (55 to 65° C.) to remove roughly 180 kg of distillate. An additional amount of toluene (180 kg) was charged to the reactor, and roughly 112 kg of solvent is distilled off under reduced pressure (55 to 65° C.). GC analysis indicated less than 0.17% THF in the vessel. The resulting mixture was cooled (0 to 5° C.) slowly (1 to 2 h) to induce precipitation of the desired product (IV). The wt. % of (IV) in the supernatant was monitored until constant (roughly 2%).

The product was filtered, rinsed with cold (0 to 5° C.) toluene (100 kg), and dried in a vacuum oven (at least 50 mm Hg vacuum, 70 to 90° C.) until constant weight was acheived (15 to 20 h). The product was isolated as a white to light yellow crystalline solid. $^1$H NMR (300 MHz; D$_6$-dmso) d 9.90 (s, 1H), 8.80 (s, 1H), 7.50 (bs, 1H), 7.45 (dd, J=2.3, 8.4 Hz, 1H), 7.39–7.36 (m, 2H), 7.28–7.23 (t, J=7.6 Hz, 2H), 7.18–7.13 (m, 1H), 6.93 (d, J=8.8 Hz, 1H), 5.24 (q, J=6.8 Hz, 1H), 1.86 (d, J=6.8 Hz, 3H). $^{19}$F NMR (282 MHz, D$_6$-dmso) d −81.8 (s). $^{13}$C NMR (75 MHz, D$_6$-dmso) d 17.9, 50.4, 84.7 (q, J=30 Hz), 115.8, 117.0, 124.0 (q, J=290 Hz), 124.9, 126.3, 127.0, 127.9, 131.6, 136.0, 143.3, 150.2; IR (KBr) 3408, 3060, 2931, 2834, 1658, and 1607 cm$^{-1}$; HRMS (CI; M+1) calcd. for C$_{17}$H$_{14}$ClF$_3$N$_2$O$_2$ 371.0774. Found: 371.0764. [a]$^{25}_D$ +195° (c=1.00, EtOAc). Anal. Calcd. for C, 55.07; H, 3.81; N, 7.56. Found: C, 55.33; H, 3.80; N, 7.51; DSC 240 to 250° C. decomposition.

EXAMPLE 2

Preparation of Quinazoline (VII) from Quinazolone (IV)

A vessel was charged with 2M n-Butylmagnesium chloride in THF (three to four equivalents relative to (IV)) and a 5% molar excess of cyclopropylacetylene (CPA) was added over 1–3 hours at a reaction temperature of 30–40° C. in order to form a 2M solution of CPA-MgCl. Butane was allowed to escape through a condenser set at 0–5° C. After addition was complete the reaction was allowed to age for 2–3 hours at 35° C., followed by cooling to 20° C.

A low temperature reactor was charged with (IV) (8 kg, 21.58 moles), toluene (80 L; 10 L per kg (IV)) and triethylamine (10.9 kg, 107.72 moles; five equivalents relative to (IV)) at 20° C. The solution was cooled to between −20 to −5° C. and thionyl chloride (2.7 kg, 22.69 moles; 1.05 mole per mole of (IV)) was added over 1–2 hours. The deep orange mixture was aged for 1 hour at −5 to 0° C., and cooled to −50° C.

The 2M CPA-MgCl solution was added to the tetraene (V-a) solution over 2 to 4 h, keeping the reaction temperature below −50° C. Little product formed during the first two thirds of the addition as salts were neutralized. After about a 1 hour age period, a sample was quenched into ethanol and the percent conversion to products measured by HPLC.

The reaction solution was transferred to a larger vessel containing a 12% solution of citric acid in water (enough to neutralize the base equivalents) at 20° C. The addition rate of the cold reaction to the quench mixture was controlled to keep the water from freezing. The temperature was raised from 0 to 20° C., and the layers separated. Water was added and the resulting mixture stirred for 0.5 hours, and the layers separated. The aqueous layers contained only traces of product and had a pH of 5 to 7. The organic layer was concentrated by distillation to 30% of its starting volume, which removed CPA, THF, water, and most of the toluene. During this distillation the product began to crystallize. Methanol was added over 1–3 hours while distilling the toluene-methanol azeotrope to half the starting volume, and a solvent composition of about 2% toluene-methanol. For convenience, the methanol for the solvent exchange was added in two portions. The slurry was cooled slowly from 63 to 20° C., and the concentration of (VII) in the supernatent analyzed. The slurry was cooled further to 5° C. over 1–3 hours, aged for 1 hour, and filtered. The product was rinsed with cold methanol and dried in a vacuum oven at 40–45° C. to give 7.7 kg (VII) in about 85% yield. The product was >99% pure and contained only traces of diastereomer, enantiomer, and pentenyne analogs. CHN Found: C, 63.31; H, 4.31; N, 6.70; mp 212° C.; ES+MS: M+1 419/421, 3:1; UV 253 nm; IR (KBr) 3190, 3058, 2941, 2240, 1683, 1604, 1502 cm$^{-1}$; $^1$H NMR (300 MHz; D$_6$-dmso) d 10.05 (s, 1H), 7.49 (s, 1H), 7.49 (d, J=9.1 Hz, 1H), 7.29 (m, 4H), 7.18 (m, 1H), 6.97 (d, J=9.1 Hz, 1H), 5.38 (bs, 1H), 1.77 (d, J=6.8 Hz, 3H), 1.62 (bs, 1H), 0.94 (m, 2H), 0.75 (bs, 2H); $^{19}$F NMR (282 MHz; D$_6$-dmso) d −78.4 (s); $^{13}$C NMR (75 MHz; D$_6$-dmso) d −1.2, 8.3, 8.4, 19.8, 57.4(br), 64.6 (q, br), 66.2, 96.0, 115.0, 115.8, 123.8 (q, J=290 Hz), 125.0, 125.7, 125.8, 127.6, 127.9, 131.2, 136.2, 141.9, 150.0.

EXAMPLE 3

Preparation of Quinazoline (I) from Quinazoline (VII)

A 100 gallon reactor was charged with about 22 kg of (VII) and the jacket temperature was set to 0° C. The vessel was then charged slowly with 65 kg of TFA. To the solution was added 2.2 L of USP water dropwise. The mixture was warmed to ambient temperature (20 to 25° C.) and held for 1 hour. After 1 hour, a sample of the mixture was analyzed for conversion to (I).

PCT (Process Control Test): Criterion for complete conversion was >99 area % consumption of (VII) as indicated by HPLC analysis.

To the reaction mixture was added 95 kg of toluene, and the solution was cooled to 0° C. The vessel was then charged with 76.2 kg of 30 wt/vol. (10 M) aqueous NaOH while the temperature was maintained below 20° C. The mixture was stirred for 1 hour and a sample of the aqueous layer was withdrawn for a pH determination.

PCT-2: The criterion for the pH of aqueous phase was: pH 7 to 12.

The mixture was heated to 40 to 50° C., and the phases separated. Water (110 L USP) was charged and the resultant solution mixed for 30 minutes. The phases were permitted to separate at 40 to 50° C. for 30 minutes, and the aqueous phase was drained. The crude product solution was weighed, and sampled for solution yield analysis. The crude solution was charged to a distillation vessel through a 5.0 μm filter to remove any particulate matter and salts. The reaction mixture was concentrated (about 2 to 3 L/kg of solvent relative to (I)) by distillation. The solution was cooled to about 90° C. and 75 kg of heptanes were added.

The mixture was cooled to ambient temperature and sampled to determine the precipitation profile. Specifically, the mother liquors were analyzed by HPLC for wt. % (I). Typical values were about 2.0 to 4.0 wt. % at ambient temperature. The mixture was cooled to 0 to 5° C. and sampled at 1 hour intervals until the precipitation profile was acceptable. When the final wt. % was <1.0 wt. %, the precipitation was determined to be complete.

The product was filtered and the mother liquors removed under vacuum for 15 minutes. The cake was washed with 40 kg of cold (0° C.) heptanes and dried on the filter for 30 minutes. The product was tranfered to trays and oven dried at 90° C. under 50 mm Hg vacuum until a constant weight was achieved. Final yield was about 80%; to provide 13.2 kg of compound (I).

The following examples exemplify the preparation of Form 1 and Form 2 of (−)-6-Chloro-4-cyclopropylethynyl-4-trifluoromethyl-3,4-dihydro-2(1H)-quinazolinone. The examples are meant to be illustrative of the present invention, and not should not be taken as limiting the inventors scope.

EXAMPLE 4

Formation of the Methanol Solvate of (I) (Form 1) from Crude (I); Followed by Polymorphic Conversion to Crystalline (I) (Form 2).

A 22 L reactor was charged with 5.2 kg of crude (I) and 13 L of methanol was slowly added. A small heat of salvation was observed estimated as about 5° C. increase per 100 grams. The mixture was heated to 60–65° C. The solids did not completely dissolve. The slurry was held at this temperature for 1 hour. The heterogeneous solution thinned during this heating period. The mixture was cooled to ambient temperature over 2 hours and the mother liquors were sampled for initial wt. % (I). The solution was cooled to −10° C. and sampled at 1 hour intervals until the crystallization profile stabilized. The solution was aged for about 4 hours afterwhich the mother liquors contained less than 3.0 wt. % (I). The product was filtered. The mother liquors were weighed and sampled for wt. % (I). The filter cake was washed twice with 15 L protions of heptanes, and dried on the filter for 30 minutes.

Polymorphic Conversion

The product was placed under vacuum at 90° C. for 12 hours and then sampled by DSC in order to monitor the polymorphic conversion. The DSC trace showed no traces of a lower melting polymorph. The solids were cooled to ambient temperature and delumped.

EXAMPLE 5

Formation of the Methanol Solvate of (I) (Form 1) in One Pot Following Ionization of (VII); Followed by Conversion to Crystalline (I) (Form 2).

A reactor was charged with 96% formic acid (250 mL), followed by (VII) (50 g, 19.39 mmol). The resulting slurry was heated to about 60 to 65° C., held for about 2 h, and the temperature decreased to roughly 40° C. PCT: <0.5 area % of (VII) by HPLC at 245 nm at about 1000 mAu. Toluene (250 mL) was charged to the reactor, followed by water (250 mL), and the resulting mixture warmed to 35 to 40° C. The mixture was stirred for about 0.5 hours, and held static for about 0.5 hours, and the phases separated.

Water (250 mL) was charged to the reactor, and the mixture was warmed to 35 to 40° C. The mixture was stirred for about 0.5 h and held static for about 0.5 hours. The phases were separated and the pH found to be about 2. The volume was about 5 L.

A low pressure distillation was performed at 60 to 65° C., to an end volume of about 100 mL. The vacuum was broken and the vessel was slowly charged with methanol (375 mL) with the use of an addition funnel. Atmospheric distillation was carried out at between 63 to 64° C., to an end volume of about 100 mL. Methanol (200 mL) was charged, and the distillation was resumed to an end volume of about 100 mL. The mixture was held at about 60° C. to assure that the solids did not crash out of solution. A sample was submitted for G.C. solvent composition analysis. The solution met the criteria of <1.2 V % toluene by GC.

The temperature was held at 60° C. for about 2 hours, followed by cooling over a 2 hour period to about 0 to 5° C. The mixture was held at this temperature while a sample of the solution was analyzed for wt % (I). The solution contained <4.2 wt % (I), and the batch was filtered. The cake was washed with room temperature heptane (200 mL). The house vacuum was pulled on the cake for about 1 hour, afterwhich the cake was distributed on a tray with about a 1 to 1.5 inch depth.

Polymorphic Conversion

The tray from the foregoing procedure was placed in the oven, a vacuum was established at room temperature and was held for about 2 hours. The temperature was then raised to 90° C., and held for about 2 hours. The temperature was then raised to about 120° C. for about 2 hours, afterwhich a small sample was removed (0.2 to 0.5 g). The sample was lightly ground to a uniform consistency with a mortar and pestle, and submitted for DSC and XRD analysis. The isolated solids had a weight of 31.8 g; equivalent to an 85% yield.

EXAMPLE 6

Formation of the Toluene/Heptane Solvate of (−)-6-Chloro-4-cyclopropylethynyl-4-trifluoromethyl-3,4-dihydro-2(1H)-quinazolinone; Compound of Formula (I).

Figure 3:
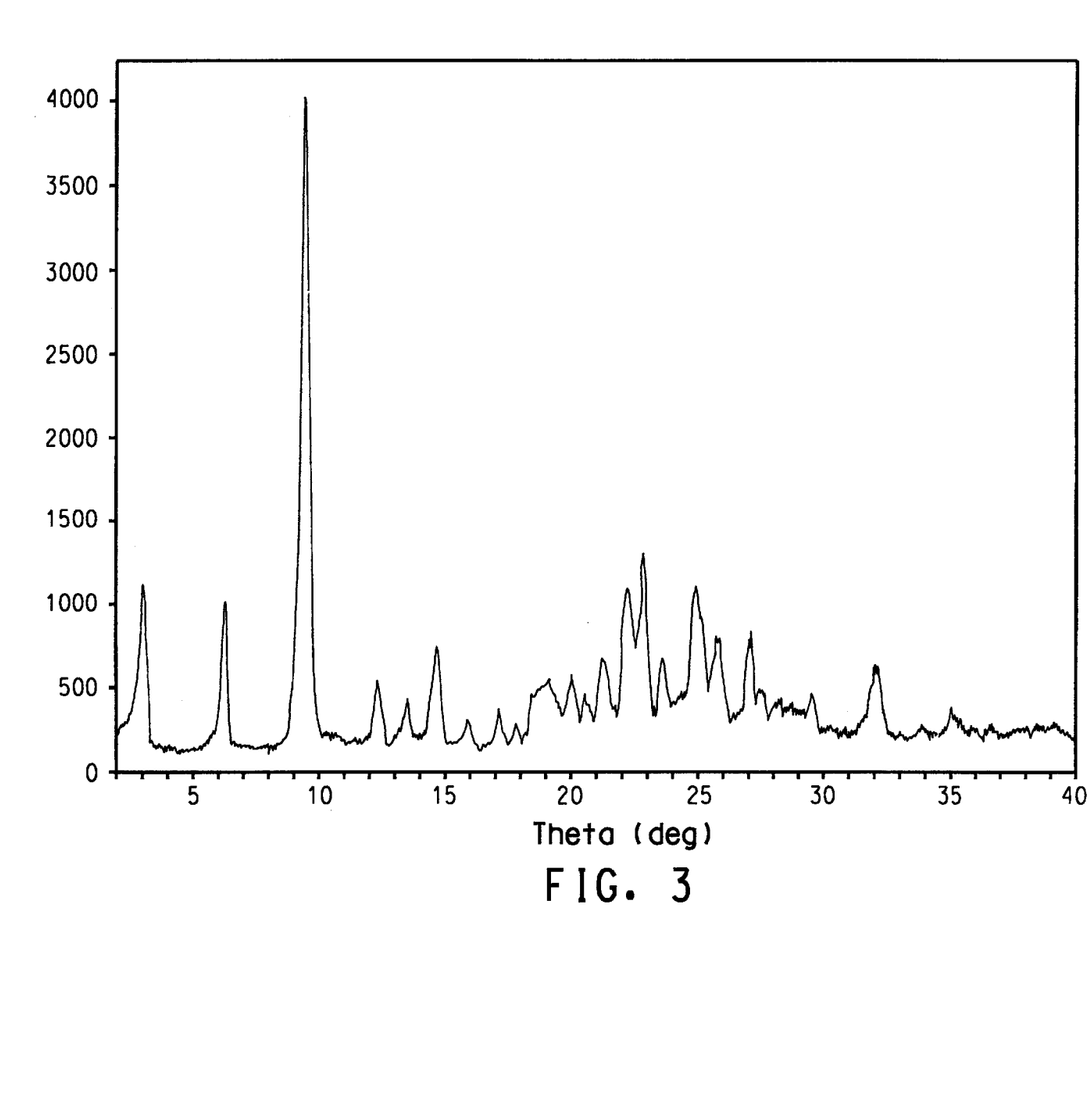
FIG. 3 shows a powder x-ray diffractogram as a toluene/heptane solvate of (-)-6-Chloro-4-cyclopropyl-ethynyl-4-trifluoromethyl-3,4-dihydro-2(1H)-quinazolinone.

A 100 L reactor is charged with formic acid (152.5 kg, 98%) and (VII) (25 kg). The mixture is heated to 60 to 65° C. and held for about 3 h. Compound (VII) typically dissolves after 45 min. at 60 to 65° C. The solution is sampled for conversion to compound (I) (criterion <0.5 area % (VII)). If the criterion is not met the solution is held for 30 min. and sampled for analysis. Toluene (108.4 kg) and purified water (125 L) are added and the mixture cooled to 40 to 50° C. The phases are separated and the organic layer is washed with water (125 L) twice. Sample the organic layer (criterion pH >2.5). If the criterion is not met perform an additional water wash. Concentrate the solution by atmospheric distillation to about 120 L and sample the solution for determination of water content (criterion <500 ppm water). If the criterion is not met add 50 kg of toluene and concentrate to 120 L. The solution is clarified and the transfer line chased with 10 kg of toluene. The solution is distilled to 63 L (about 2.0 to 2.5 L/kg toluene to (I)) and cooled to 90 to 95° C. Heptanes 94.1 kg is added while maintaining the temperature above 85° C. If the batch temperature falls below 80° C. (I) will precipitate. The solution is sampled for solvent composition (criterion <30 v/v % toluene in heptanes). If the solvent criterion is not met additional solvent is added to achieve the desired composition. The solution is cooled to 20° C. over 5 h and the "wet cake" assayed for area purity (criterion >98 area % (I)). If the purity criterion is met, the slurry is cooled to 0° C. and held for 1 h. If the purity criterion is not satisfied isolate the product at 20° C. Crude (I), which does not meet the purity criterion of may need to be reprocessed by crystallization. The mother liquors are sampled and assayed for (I) content (criterion <1.0 wt. % (I)). If the criterion is not met hold for an additional 1 h and sample. Compound (I) is isolated by filtration and the filter cake was washed with 2×34.2 kg portions of cold (<0° C.) heptanes. The "wet cake" is dried on the filter for 30 minutes, then dried under vacuum at 80° C. and held until a LOD of <2.0% is achieved (criterion: LOD of ≦2.0%). The expected yield is 85% (15.9 kg) of (I). The typical purity is ≦98% area (I). DSC Transition at 113° C. Characteristic XRPD Peaks (2θ°): 3.1°, 6.3°, 9.5°, and 12.3°. FIG. 3 illustrates a characteristic powder x-ray diffractogram from 0 to 40 degrees in 2 theta of (−)-6-chloro-4-cyclopropyl-ethynyl-4-trifluoromethyl-3,4-dihydro-2 (1H)-quinazolinone as a toluene/heptane solvate.

EXAMPLE 7

Formation of the Formic Acid Solvate of (−)-6-Chloro-4-cycloproylethynyl-4-trifluoromethyl-3,4-dihydro-2(1H)-quinazolinone: Compound of Formula (I).

Figure 4:
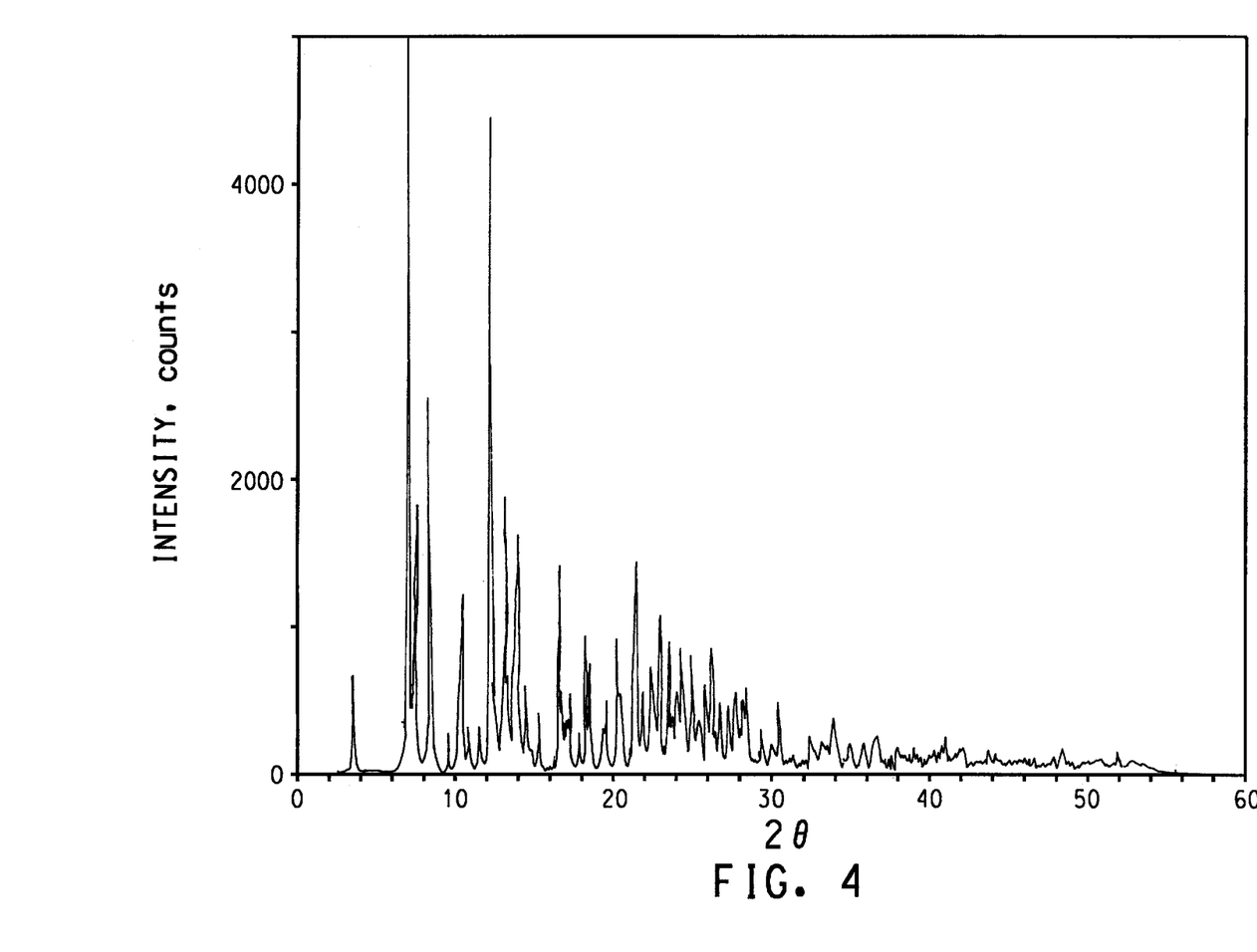
FIG. 4 shows a powder x-ray diffractogram as a formic acid solvate of (-)-6-Chloro-4-cyclopropyl-ethynyl-4-trifluoromethyl-3,4-dihydro-2(1H)-quinazolinone.

Following the procedure of Example 6, a 100 L reactor is charged with formic acid (152.5 kg, 98%) and (VII) (25 kg). The mixture is heated to 60 to 65° C. and held for about 3 h. Compound (VII) typically dissolves after 45 min. at 60 to 65° C. The solution is sampled for conversion to compound (I) (criterion <0.5 area % (VII)). If the criterion is not met the solution is held for 30 min. and sampled for analysis. After satisfactory conversion of (VII) to (I), the solution is cooled to 20° C. and held while (I) crystallizes from solution. FIG. 4 illustrates a characteristic powder x-ray diffractogram from 0 to 60 degrees in 2 theta of (−)-6-chloro-4-cyclopropyl-ethynyl-4-trifluoromethyl-3,4-dihydro-2(1H)-quinazolinone as a formic acid solvate.

ANALYTICAL METHODS

Achiral HPLC

HPLC Column: Zorbax SB C-18, 25 cm, 50° C., 250 nm, flow 1.1. A: $H_2O$ (0.05% TFA) B: $CH_3CN$. 60% B to 90% in 5 min. to 95% in 6 min., stop time 9 min. Retention times: (IV), 3.9 min.; diastereomer of (IV), 3.8 min.; (VII), 6.4 min.; toluene, 4.5 min.; diastereomer of (VII), 6.5 min.; isomer of (VII), 6.2 min.

Chiral HPLC

HPLC Eclipse column XDB C-18, 25 cm×4.6 mm id; mobile phase acetonitrile—10 mM $NaH_2PO_4$ buffer, pH3.6, 40° C., flow 1.5 mL/min., 35% $CH_3CN$ to 95% in 15 min.; 245 nm, inj vol 5 uL, stop time 20 min., post time 3 min. Retention times: (IV), 8.8 min.; diastereomer of (VI), 8.5 min.; (VII), 13.3 min.; diastereomer of (VII), 13.5 min.

x-Ray Powder Diffraction x-Ray powder diffraction data of Forms 1 and 2 of (I) were obtained with a Philips Model 3720 automated powder diffractometer. Samples were run in a batch mode with a Model PW 1775 multi-position sample changer. The diffractometer was equipped with a variable slit (q-compensating slit), a scintillation counter and a graphite monochromator. The radiation was CuKa (40 kV, 30 mA). Data were collected at room temperature from 2 to 60 degrees 2 theta; the step size was 0.02 degrees; the count time was 0.5 sec. per step. Samples were prepared on glass specimen holders as a thin layer of powdered material without solvent.

Differential Scanning Calorimetry

The thermal properties of Forms 1 and 2 of (I) were characterized with differential scanning calorimetry using a TA Instruments DSC 910, with data analysis via a TA Instruments Thermal Analyzer 2100. Samples were placed in sealed aluminum pans for analysis with an empty aluminum pan serving as the reference. Heating rates of 5° C. per minute or 10° C. per minute were employed over a temperature range of 25° C. to 200° C. The instrumennt was calibrated with an indium standard.

Nuclear Magnetic Resonance Spectroscopy

¹H NMR spectra were aquired on a 300 MHz spectrometer at ambient temperature. Approximately 10 mg of sample were dissolved in $CDCl_3$ for the aquisition of the spectra. Chemical shifts were reported on a TMS scale.

What is claimed is:

1. Crystalline (−)-6-chloro-4-cyclopropylethynyl-4-trifluoro-methyl-3,4-dihydro-2(1H)-quinazolinone in solvate form.

2. The compound of claim 1, wherein the solvate form is the methanol solvate.

3. The compound of claim 2, which is characterized by an x-ray powder diffraction pattern comprising two or more 2θ values selected from the group consisting of: 9.26±0.2, 12.00±0.2, 15.02±0.2, 23.52±0.2, and 24.08±0.2.

4. The compound of claim 3, wherein the x-ray powder diffraction pattern comprises 2θ values at 9.26±0.2 and 15.02±0.2.

5. The compound of claim 2, which is characterized by an x-ray powder diffraction pattern substantially in accordance with that shown in FIG. 1.

6. The compound of claim 2, which is characterized by a differential scanning calorimetry thermogram exhibiting an endothermic transition at about 90° C. to about 110° C.

7. The compound of claim 2, which is characterized by an nuclear magnetic resonance spectrum having a singlet peak at about 3.49 ppm.

8. A pharmaceutical composition comprising a therapeutically effective amount of the compound of claim 2 and a pharmaceutically acceptable carrier.

9. A method for the treatment of human immunodeficiency virus infection which comprises administering to a host in need of such treatment a therapeutically effective amount of a compound of claim 2.

10. The compound of claim 2, prepared by recrystallization of (−)-6-Chloro-4-cyclopropylethynyl-4-trifluoromethyl-3,4-dihydro-2(1H)-quinazolinone from methanol.

11. A process for the preparation of the compound of claim 2 comprising:
   1) suspending (−)-6-chloro-4-cyclopropylethynyl-4-trifluoromethyl-3,4-dihydro-2(1H)-quinazolinone in methanol to form a suspension;
   2) heating the suspension at a temperature between about 30° C. and about 65° C.;
   3) cooling the suspension at temperature between about −20° C. and about 0° C. to form a compound of claim 2; and
   4) filtering the compound of claim 2.

12. Form 2 of crystalline (−)-6-Chloro-4-cyclopropylethynyl-4-trifluoromethyl-3,4-dihydro-2(1H)-quinazolinone.

13. The compound of claim 12, which is characterized by an x-ray powder diffraction pattern comprising three or more 2θ values selected from the group consisting of: 10.41±0.2, 11.25±0.2, 11.61±0.2, 19.46±0.2, 19.88±0.2, 22.17±0.2, 22.89±0.2, 25.57±0.2, and 26.38±0.2.

14. The compound of claim 12, which is characterized by an x-ray powder diffraction pattern substantially in accordance with that shown in FIG. 2.

15. The compound of claim 12, which is characterized by a differential scanning calorimetry thermogram having a peak at about 183° C. to about 186° C.

16. A pharmaceutical composition comprising a therapeutically effective amount of the compound of claim 12 and a pharmaceutically acceptable carrier.

17. The pharmaceutical composition of claim 16 contained in a capsule or compressed tablet dosage form.

18. The pharmaceutical composition of claim 16, contained in a capsule or compressed tablet dosage form wherein the therapeutically effective amount is about 1 mg to about 1000 mg per dose.

19. The pharmaceutical composition of claim 16 in liquid form.

20. A method for the treatment of human immunodeficiency virus infection which comprises administering to a host in need of such treatment a therapeutically effective amount of a compound of claim 12.

21. A method of treating HIV infection which comprises administering, in combination, to a host in need thereof a therapeutically effective amount of:
   (a) a compound of claim 12; and
   (b) at least one compound selected from the group consisting of HIV reverse transcriptase inhibitors and HIV protease inhibitors.

22. A process for the preparation of the compound of claim 12 comprising:
   1) heating (−)-6-chloro-4-cyclopropylethynyl-4-trifluoromethyl-3,4-dihydro-2 (1H)-quinazolinone in solvate form at a temperature between about 85° C. and about 100° C.; followed by
   2) heating the product of step 1 at a temperature between about 115° C. and about 130° C. to form a compound of claim 12.

23. The process of claim 22 further comprising:
   1) heating (−)-6-chloro-4-cyclopropylethynyl-4-trifluoromethyl-3,4-dihydro-2(1H)-quinazolinone in methanol form at a temperature between about 85° C. and about 100° C. for about 1 hour to about 3 hours; followed by
   2) heating the product of step 1 at a temperature between about 115° C. and about 130° C. for about 1 hour to about 3 hours to form a compound of claim 12.

24. A pharmaceutical composition comprising the crystalline form of claim 1, the crystalline form of claim 12, or mixtures thereof, and a pharmaceutically acceptable carrier.

* * * * *